United States Patent [19]

Beauquey et al.

[11] Patent Number: 5,846,549

[45] Date of Patent: Dec. 8, 1998

[54] DETERGENT COSMETIC COMPOSITIONS COMPRISING CLAY

[75] Inventors: Bernard Beauquey, Clichy; Sandrine Decoster, Epinay Sur Seine, both of France

[73] Assignee: L'Oreal, Paris, France

[21] Appl. No.: 407,703

[22] Filed: Mar. 21, 1995

[30] Foreign Application Priority Data

Mar. 22, 1994 [FR] France .................................. 94-03329

[51] Int. Cl.$^6$ .............................. A61K 7/48; A61K 7/075
[52] U.S. Cl. ..................... 424/401; 424/70.1; 424/70.19; 424/70.21; 424/70.22; 424/70.7; 424/70.31; 514/938; 514/949
[58] Field of Search .................................. 424/401, 70.19, 424/70.1, 70.21, 70.22, 70.27, 70.31; 514/938, 949

[56] References Cited

U.S. PATENT DOCUMENTS 4,874,868 10/1989 Bolich ...................................... 548/110
5,536,493 7/1996 Dubief et al. ........................ 424/70.13

FOREIGN PATENT DOCUMENTS

| A-0331833 | 9/1989 | European Pat. Off. . |
| 3206448 | 10/1982 | Germany . |
| A-3206448 | 10/1982 | Germany . |
| 2011786 | 7/1979 | United Kingdom . |

OTHER PUBLICATIONS

Derwent Abstract of DE–A–3206448.

Derwent Abstract of JP–5310539.

*Primary Examiner*—Jyothsan Venkat
*Attorney, Agent, or Firm*—Finnegan,Henderson, Farabow, Garrett & Dunner, L.L.P.

[57] ABSTRACT

Novel cosmetic compositions intended for cleaning the hair, the scalp and/or the skin, based on detergent surfactants, silicone and clay are disclosed. These compositions may be used for example as shampoos or shower gels.

27 Claims, No Drawings

DETERGENT COSMETIC COMPOSITIONS COMPRISING CLAY

The present invention is directed to novel cosmetic compositions that are oil-in-water emulsions intended for cleaning the hair, the scalp and/or the skin, which are based on detergent surfactants, silicone and clay. The present invention is also directed to the use of such compositions in cosmetic applications.

Detergent cosmetic compositions, shampoos or shower gels for example, containing both surfactants with washing power and one or more conditioners, are commonly used for cleaning the hair and/or the skin.

In fact, to improve the cosmetic properties of detergent compositions, and more particularly those intended for application to sensitized hair, i.e., hair which has been damaged or embrittled, especially under the chemical action of atmospheric agents and/or hair treatments such as perming, dyeing or bleaching, it is frequently necessary to introduce into the compositions complementary cosmetic agents such as, for example, silicones, which then make the treated hair easy to disentangle and style, as well as greatly enhancing its softness and luster.

Because of the insoluble character of these silicones in the aqueous media used in shampoos, attempts are made to keep the silicones in dispersed form. This dispersed form enables the silicone to deposit on the hair or the skin and not be totally removed during rinsing. It is important, however, that the suspension process does not disturb the detergent and foaming properties of the cosmetic composition.

There are currently only a few effective means of keeping insoluble silicones in suspension; this being a difficult problem to solve. It has already been proposed to use long-chain ester or ether derivatives (pearlescent agents) or polysaccharides such as xanthan gum (gelling agents) for this purpose. However, pearlescent agents present crystallization problems which cause the viscosity of the compositions to change, i.e., increase, with time. Gelling agents also have disadvantages, namely, on the one hand, that detergent compositions containing xanthan gum do not easily develop foam (poor initial foam formation) and, on the other hand, that the compositions trickle because they do not have a smooth texture, a feature not liked by consumers.

It has also been proposed, in Japanese Patent Application No. J05310539, to use water-soluble non-ionic polymers to stabilize a composition containing a surfactant and water-insoluble particles like clays and silicone oil. However, J05310539 does not teach the use of a clay as a suspension agent for the silicone oil.

The use of a water-in-oil type emulsified composition to keep insoluble silicones in suspension has been proposed in European Patent Application No. 331833. European Patent Application No. 331833 discloses an emulsified water-in-oil type composition which contains a water-swellable clay mineral, a non-ionic surfactant, an oil component and water as essential constituents. The composition of EPA 331833 has, as such, an oil-based vehicle, i.e., a water-in-oil emulsion, and does not have an aqueous vehicle, i.e., an oil-in-water emulsion.

An object of the present invention is to propose a novel means of keeping insoluble silicones in suspension in shampoos.

It has now been discovered that by introducing a clay into oil-in-water emulsion detergent cosmetic compositions based on surfactants and silicone, it is possible to keep the insoluble silicones in suspension.

The compositions according to the invention are stable; in particular, there is no graining-out of the silicone or uncontrolled thickening of the composition over time. Moreover, the foaming properties, such as the initial foam formation, are not impaired. The washing properties and the other advantageous cosmetic properties, i.e., softness, disentangling, and styling which are associated with these compositions are also preserved. Finally, the compositions according to the invention have a soft, creamy and non-stringy texture. All these discoveries form the basis of the present invention.

Thus, in accordance with the present invention, novel detergent cosmetic compositions are now provided which comprise an oil-in-water emulsion, the emulsion including a cosmetically acceptable aqueous medium, at least one detergent surfactant, at least one insoluble silicone, and at least one clay, wherein the compositions do not contain xanthan gum or water-soluble non-ionic polymers. The detergent cosmetic compositions of the invention are oil-in-water emulsions, and are not water-in-oil emulsions.

The present invention is also directed to the use of the above compositions in cosmetics for cleaning the hair, the skin and/or the scalp.

The present invention further relates to a method for the preparation of a detergent cosmetic composition which comprises using a clay as an agent for dispersing an insoluble silicone in a detergent cosmetic composition, wherein the composition is an oil-in-water emulsion which contains at least one insoluble silicone and at least one detergent surfactant; in other words, the clay is a suspension agent for the insoluble silicone, such as silicone oil.

Other characteristics, features and advantages of the invention will become even more clearly apparent from the following description and from the concrete but non-limiting examples which are intended to illustrate it.

The nature of the surfactants forming part of the detergent compositions according to the invention is not critical. The detergent surfactants which can be used according to the invention are preferably of the anionic, non-ionic, amphoteric, zwitterionic or cationic type. It is also preferable to use one or more anionic surfactants or a mixture of anionic surfactants and amphoteric, zwitterionic or non-ionic surfactants.

Thus, as examples of anionic surfactants which can be used, by themselves or in mixtures, within the framework of the present invention, there may preferably be mentioned salts, in particular alkali metal salts, especially sodium salts, ammonium salts, amine salts, amino alcohol salts or magnesium salts, of the following compounds: alkylsulphates, alkyl-ether-sulphates, alkylamido-ether-sulphates, monoglyceride-sulphates, alkylglycerylsulphonates, alkylsulphonates, alkylphosphates, alkylamidesulphonates, alkylarylsulphonates, α-olefin-sulphonates, alkylsulphosuccinates, alkyl-ether-sulpho-succinates, alkylamidesulphosuccinates, alkylsulphosuccinamates, alkylsulphoacetates, alkyl-ether-phosphates, acylisethionates, and N-acylamino acids such as N-acylsarcosinates, N-acylglutamates and N-acyltaurates. Among the other anionic surfactants which can be used, there may also be mentioned fatty acid salts such as the salts of undecylenic, oleic, ricinoleic, palmitic and stearic acids and the acids of copra oil or hydrogenated copra oil, and acylhydroxy acids such as acyllactylates. It is also possible to use weakly anionic surfactants such as alkyl-D-galactosideuronic acids and salts thereof, as well as poly-alkoxylated carboxylic ether-acids, in particular those containing from 2 to 24 ethylene oxide groups, and mixtures thereof (the alkyl or acyl radical of all these different compounds preferably containing from 8 to 22 carbon atoms).

Non-ionic surfactants which may preferably be used in accordance with the present invention are polyethoxylated, polypropoxylated or polyglycerolated fatty alcohols, alphadiols, alkylphenols or acids having a fatty chain containing from 8 to 28 carbon atoms; it being possible for the number of ethylene oxide or propylene oxide groups to range from 2 to 50 and for the number of glycerol groups to range from 2 to 30 in particular. There may also be mentioned ethylene oxide/propylene oxide copolymers, condensation products of ethylene oxide and propylene oxide with fatty alcohols, polyethoxylated fatty amines or amides preferably having from 2 to 30 moles of ethylene oxide, polyglycerolated fatty amides containing an average of from 1 to 5 glycerol groups, polyglycerolated diglycolamides, optionally ethoxylated fatty acid esters of sorbitan, fatty acid esters of sucrose, polyalkoxylated fatty acid esters, optionally alkoxylated alkylpolyglycosides, alkylglucoside esters, derivatives of N-alkylglucamines and of N-acylmethylglucamines, and amine oxides.

Amphoteric or zwitterionic surfactants which may preferably be used in accordance with the present invention are secondary or tertiary aliphatic amine derivatives in which the aliphatic radical is a linear or branched chain containing from 8 to 22 carbon atoms and containing at least one water-solubilizing anionic group, for example, carboxylate, sulphonate, sulphate, phosphate or phosphonate. There may be mentioned alkylbetaines, alkyldimethylbetaines, alkylsulphobetaines, alkylamidoalkylbetaines, alkylamidoalkylsulphobetaines, and imidazoline derivatives such as amphocarboxyglycinate or amphocarboxypropionate derivatives.

The surfactant or surfactants are preferably present in the compositions according to the invention in proportions which preferably range from 5 to 50% by weight, and more preferably from 5 to 20% by weight, based on the total weight of the composition. The insoluble silicones which can be used within the framework of the present invention can be selected from all those which are already known per se for improving the cosmetic properties of hair treated with detergent compositions, namely in particular those described in European Patent Applications EP-A-0181773 and EP-A-0473508, the disclosures of which are incorporated herein by reference. It is of course possible to use mixtures of silicones.

Thus, according to the present invention, it is possible to use any silicone known per se, whether it be a silicone oil, a silicone resin or a silicone gum. Silicones are organosilicon polymers or oligomers of linear or cyclic, branched or crosslinked structure and of variable molecular weight, obtained by the polymerization and/or polycondensation of appropriately functionalized silanes and consisting essentially of a repetition of principal units in which the silicon atoms are joined together by oxygen atoms, via a siloxane bond, optionally substituted hydrocarbon radicals being directly bonded to said silicon atoms via a carbon atom. The most common hydrocarbon radicals are alkyl radicals, in particular methyl, fluoroalkyl radicals, aryl radicals, in particular phenyl, and alkenyl radicals, in particular vinyl. Other types of radicals which may be bonded to the siloxane chain, either directly or via a hydrocarbon radical, are especially hydrogen, halogens, in particular chlorine, bromine or fluorine, thiols, alkoxy radicals, polyoxyalkylene (or polyether) radicals, in particular polyoxyethylene and/or polyoxypropylene, hydroxyl or hydroxyalkyl radicals, substituted or unsubstituted amino groups, amide groups, acyloxy or acyloxyalkyl radicals, hydroxyalkylamino or aminoalkyl radicals, quaternary ammonium groups, amphoteric or betaine groups, and anionic groups such as carboxylates, thioglycolates, sulphosuccinates, thiosulphates, phosphates and sulphates; it being understood that this list in no way implies a limitation, in other words, all so-called "organomodified" silicones are useful in the present invention. In general terms, the silicones which are preferably used within the framework of the present invention are those described in "Encyclopedia of Chemical Technology," Kirk-Othmer, Third Edition, 1982, volume 20, pp. 922 et seq. and in "Chemistry and Technology of Silicones," Walter NOLL, Academic Press Inc., San Diego Calif., 1968, the disclosures of which are incorporated herein by reference. It is also possible to use linear block copolymers comprising polysiloxane segments in their main chain, such as, for example, polysiloxane-polyoxyalkylene or polysiloxane-polyurethane and/or polyurea block copolymers. The average molecular weight of the silicones which can be used according to the invention preferably ranges from 100 to several million, and more preferably ranges from 1,000 to 1,000,000. According to the present invention, it is of course possible either to use one silicone or to use several different silicones.

As examples of silicones which can preferably be used in the detergent compositions according to the invention, there may be mentioned especially polydialkylsiloxanes, polyalkylarylsiloxanes, polydiaryldialkylsiloxanes and, even more generally, all the organopolysiloxanes described in the patent application published under the number WO 93/05762, whose disclosure is incorporated herein by reference.

In a particularly preferred embodiment of the present invention, the silicones used are selected from diorganopolysiloxanes (oils, gums or resins), preferably from optionally modified polydialkylsiloxanes or polyalkylarylsiloxanes, and even more preferably from optionally modified polydimethylsiloxanes. Silicone gums are particularly preferred, especially those of optionally modified polydialkylsiloxanes or polyalkylarylsiloxanes. They can be used by themselves or in a mixture in a solvent selected for example from volatile silicones, polydimethylsiloxane or polyphenylmethylsiloxane oils, isoparaffins, pentane, dodecane and mixtures thereof.

The silicone or silicones may be present in the compositions according to the invention in proportions preferably ranging from 0.01 to 10% by weight, and more preferably from 0.5 to 5% by weight, based on the total weight of the composition.

According to an essential characteristic of the detergent cosmetic compositions according to the invention, the compositions contain at least one clay which is natural or synthetic, but preferably natural. The detergent compositions according to the invention can of course contain one clay or a mixture of clays.

Clays are products already well known per se, which are described for example in the work "Minéralogie des argiles" (Mineralogy of clays), S. Caillère, S. Hénin, M. Rautureau, 2nd edition 1982, Masson, whose disclosure is incorporated herein by reference.

The families of clays which may preferably be used in accordance with the present invention include; kaolinite, such as dickite and nacrite, halloysite, dombassite, antigorite, benthierine, pyrophyllite, montmorillonite, beidellite, vermiculite, talc, stevensite, hectorite, saponite, chlorite and sepiolite and mixtures thereof.

The clays can also be chemically modified with various compounds such as acrylic acids, polysaccharides, for example carboxymethyl cellulose, or organic cations.

The chosen clays will preferably be those which are cosmetically compatible and acceptable for use on the hair, the skin and/or the scalp.

In a particularly preferred embodiment of the present invention, the clay used is selected from kaolinites, montmorillonites, hectorites and mixtures thereof.

In accordance with the present invention, it is preferable to use a mixture of clays from different families. It is even more preferable to use a mixture of at least one clay of the kaolinite family and at least one clay of the montmorillonite family. When a mixture of kaolinites and montmorillonites is used, the ratio, by weight, of kaolinites to montmorillonites preferably ranges from 0.75 to 10, and more preferably ranges from 0.75 to 3.

According to the invention, the clay or clays may be present in the compositions in an amount preferably ranging from 0.5 to 15% by weight, more preferably from 2 to 10% by weight, and even more preferably from 4 to 8% by weight, based on the total weight of the composition.

The vehicle or carrier of the detergent compositions according to the invention is preferably water or an aqueous-alcoholic solution, for example containing a lower alcohol such as ethanol, isopropanol or butanol.

The detergent compositions according to the invention have a final pH preferably ranging from 4 to 8. The final pH more preferably ranges from 5 to 7. The pH can be adjusted to the desired value in a conventional manner by the addition, as appropriate, of either alkalizing agents or acidifying agents which are conventionally used and known to be cosmetically acceptable.

The detergent compositions according to the invention can of course also contain all the adjuvants normally encountered in the field of hair and/or body shampoos, such as, for example, perfumes, preservatives, sequestering agents, acidifying agents, alkalizing agents, thickeners other than clay, softeners, foam modifiers, colourants, pearlescent agents, moisturizers, antidandruff or antiseborrhoea agents, vitamins, sun filters, polymers, preferably cationic or amphoteric polymers, and the like.

These compositions can be presented in the form of liquids, thickened to a greater or lesser degree, cremes or gels and they are mainly suitable for washing the hair and/or the skin.

Concrete examples will now be given to illustrate the invention.

EXAMPLE 1

A shampoo according to the invention was prepared which had the following composition:

| | |
|---|---|
| Sodium lauryl-ether-sulphate containing 2.2 moles of ethylene oxide | 9.8 g |
| Sodium cocoamidoethyl(N-hydroxyethyl, N-carboxymethyl)glycinate sold under the name MIRANOL C2M by RHONE-POULENC | 3.8 g |
| Polydiinethylsiloxane (PDMS) (Oil 47 V 500.000 RHONE-POULENC) | 1 g |
| Kaolinite (KAOLIN SUPREME 1 from ETS ERNEST ORTMANS) | 7 g |
| Preservatives, colourants, perfume qs | |
| Water qsp | 100 g |

The pH of this shampoo was adjusted to 5.5 by the addition of citric acid.

This shampoo composition was stable, the silicones were kept perfectly in suspension and the viscosity did not change with time.

This composition was applied to wet hair and the hair was massaged; the foam developed immediately, in contrast to a composition containing 1% of xanthan gum in place of the clay.

EXAMPLE 2

A shampoo according to the invention was prepared which had the following composition:

| | |
|---|---|
| Sodium lauryl-ether-sulphate containing 2.2 moles of ethylene oxide | 9.8 g |
| Cocoylbetaine | 2.24 g |
| Mixture (13/87) of a PDMS gum and cyclomethicone (Q2-1401 from DOW CORNING) | 2.5 g |
| Montmorillonite (GELWHITE HNF from ECC INTERNATIONAL) | 4 g |
| Crosslinked ($C_{10}/C_{30}$)alkyl acrylate/acrylic acid copolymer (CARBOPOL 1382 from GOODRICH) | 0.2 g |
| Preservatives, colourants, perfume qs | |
| Water qsp | 100 g |

The pH of this shampoo was adjusted to 5 by the addition of citric acid.

This shampoo composition had the same properties as that of Example 1.

EXAMPLE 3

A shampoo according to the invention was prepared which had the following composition:

| | |
|---|---|
| Sodium lauryl-ether-sulphate containing 2.2 moles of ethylene oxide | 9.8 g |
| Sodium cocoamidoethyl(N-hydroxyethyl, N-carboxymethyl) glycinate sold under the name MIRANOL C2M by RHONE-POULENC | 3.2 g |
| Mixture (33/67) of a PDMS gum (PM 500 000) and PDMS oil (viscosity 1 000 cst) sold under the name silicone CF 1 241 by GENERAL ELECTRIC | 3 g |
| Montmorillonite (GELWHITE HNF from ECC INTERNATIONAL) | 4 g |
| Kaolinite (KAOLIN SUPREME 1 from ETS ERNEST ORTMANS) | 5 g |
| Preservatives, colourants, perfume qs | |
| Water qsp | 100 g |

The pH of this shampoo was adjusted to 5 by the addition of citric acid.

This shampoo composition had the same properties as that of Example 1.

What is claimed is:

1. A detergent cosmetic composition comprising an oil-in-water emulsion, said emulsion including a cosmetically acceptable aqueous medium, at least one detergent surfactant, at least one insoluble silicone wherein said insoluble silicone is silicone gums, silicone resins, mixtures of silicone gums and silicone oils, mixtures of silicone gums and silicone resins, or mixtures of silicone resins and silicone oils, and at least one clay, wherein said composition does not contain xanthan gum or water-soluble non-ionic polymers.

2. A composition according to claim 1, wherein said at least one clay is present in an amount which ranges from 0.5 to 15% by weight, based on the total weight of the composition.

3. A composition according to claim 2, wherein said at least one clay is present in an amount which ranges from 2 to 10% by weight, based on the total weight of the composition.

4. A composition according to claim 3, wherein said at least one clay is present in an amount which ranges from 4 to 8% by weight, based on the total weight of the composition.

5. A composition according to claim 1, wherein said at least one detergent surfactant is present in an amount ranging from 5 to 50% by weight, based on the total weight of the composition.

6. A composition according to claim 5, wherein said at least one detergent surfactant is present in an amount ranging from 5 to 20% by weight, based on the total weight of the composition.

7. A composition according to claim 1, wherein said at least one insoluble silicone is present in an amount ranging from 0.01 to 10% by weight, based on the total weight of the composition.

8. A composition according to claim 7, wherein said at least one insoluble silicone is present in an amount ranging from 0.5 to 5% by weight, based on the total weight of the composition.

9. A composition according to claim 1, wherein said aqueous medium is an aqueous-alcoholic medium.

10. A composition according to claim 1, wherein the pH of said composition ranges from 4 to 8.

11. A composition according to claim 10, wherein said pH ranges from 5 to 7.

12. A composition according to claim 1, wherein said at least one detergent surfactant is anionic, non-ionic, amphoteric, or cationic.

13. A composition according to claim 12, wherein said at least one detergent surfactant is an anionic surfactant.

14. A composition according to claim 12, wherein said at least one detergent surfactant is a mixture of anionic surfactants and amphoteric, or non-ionic surfactants.

15. A composition according to claim 1, wherein said at least one clay is kaolinite, halloysite, dombassite, antigorite, benthierine, pyrophyllite, montmorillonite, beidellite, vermiculite, talc, stevensite, hectorite, saponite, chlorite, sepiolite or a mixture thereof.

16. A composition according to claim 15, wherein said at least one clay is kaolinite, montmorillonite, hectorite or a mixture thereof.

17. A composition according to claim 1, which comprises a mixture of clays.

18. A composition according to claim 17, which comprises at least one clay of the kaolinite family and at least one clay of the montmorillonite family.

19. A composition according to claim 1, wherein said at least one insoluble silicone is a polydialkylsiloxane or a polyalkylarylsiloxane.

20. A composition according to claim 19, wherein said at least one insoluble silicone is gums of modified or unmodified polydialkylsiloxanes or polyalkylarylsiloxanes.

21. A method for the preparation of a detergent cosmetic composition which comprises using a clay as an agent for dispersing an insoluble silicone wherein said insoluble silicone is silicone gums, silicone resins, mixtures of silicone gums and silicone oils, mixtures of silicone gums and silicone resins, or mixtures of silicone resins and silicone oils, in said detergent composition, wherein said composition is an oil-in-water emulsion containing at least one insoluble silicone and at least one detergent surfactant.

22. A method for the cleaning of hair, scalp and/or skin which comprises applying a composition according to claim 1 to said hair, scalp and/or skin.

23. A composition according to claim 13, wherein said anionic surfactant is a salt.

24. A composition according to claim 1, which further comprises a cosmetically acceptable adjuvant.

25. A composition according to claim 1, wherein said composition is in the form of a thickened liquid, a cream or a gel.

26. A composition according to claim 1, wherein said at least one clay is a natural clay.

27. A composition according to claim 1, wherein said at least one detergent surfactant is zwitterionic.

* * * * *